United States Patent
Msika et al.

(10) Patent No.: US 8,449,930 B2
(45) Date of Patent: May 28, 2013

(54) DRUG OR DERMATOLOGICAL COMPOSITION CONTAINING AN AVOCADO PEPTIDE EXTRACT FOR TREATING AND PREVENTING PRURITUS

(75) Inventors: Philippe Msika, Versailles (FR); Caroline Baudoin, Rambouillet (FR); Stéphanie Bredif, Chaudon (FR)

(73) Assignee: Laboratoires Expanscience, Courbevoie (FR)

( * ) Notice: Subject to any disclaimer, the term of this patent is extended or adjusted under 35 U.S.C. 154(b) by 38 days.

(21) Appl. No.: 13/128,109

(22) PCT Filed: Nov. 6, 2009

(86) PCT No.: PCT/EP2009/064785
§ 371 (c)(1),
(2), (4) Date: May 6, 2011

(87) PCT Pub. No.: WO2010/052312
PCT Pub. Date: May 14, 2010

(65) Prior Publication Data
US 2011/0217277 A1  Sep. 8, 2011

(30) Foreign Application Priority Data
Nov. 7, 2008 (FR) .................. 08 57583

(51) Int. Cl.
*A61K 36/33* (2006.01)
(52) U.S. Cl.
USPC ................................................ 424/767
(58) Field of Classification Search
None
See application file for complete search history.

(56) References Cited

U.S. PATENT DOCUMENTS

| | | | |
|---|---|---|---|
| 5,932,230 | A | 8/1999 | DeGrate |
| 2008/0113921 | A1 | 5/2008 | Piccirilli et al. |
| 2008/0194476 | A1 | 8/2008 | Piccirilli et al. |

FOREIGN PATENT DOCUMENTS

| | | |
|---|---|---|
| WO | WO/98/47479 A1 | 10/1998 |
| WO | WO/01/21150 A1 | 3/2001 |
| WO | WO/01/21605 A2 | 3/2001 |
| WO | WO 2005105123 A1 * | 11/2005 |
| WO | WO/2005/115421 A1 | 12/2005 |
| WO | WO/2007/057439 A1 | 5/2007 |
| WO | WO/2008/027533 A2 | 3/2008 |

OTHER PUBLICATIONS

Miyamoto et al, "Itch-Associated Response Induced by Experimental Dry Skin in Mice", Jpn. J. Phamacol. 88, 285-292 (2002).*
Adeyemi et al., "Analgesic and anti-inflammatory effects of the aqueous extract of leaves of *Persea americana* Mill (Lauraceae)", Fitoterapia, 2002, 73:375-380.
International Search Report issued for application No. PCT/EP2009/064785 on Jun. 12, 2010.
Weisshaar et al., "Pruritus in pregnancy and childhood—do we really consider all relevant differential diagnoses?", *European Journal of Dermatology*, 2005, vol. 15, (5):320-31.

* cited by examiner

*Primary Examiner* — Chris R Tate
*Assistant Examiner* — Deborah Davis
(74) *Attorney, Agent, or Firm* — Foley & Lardner LLP

(57) ABSTRACT

The invention relates to a drug or a dermatological composition containing an avocado peptide extract for treating and/or preventing pruritus, in particular gravidic pruritus, pruritus sine materia, pruritus in newborns, and pruritus originating from a drug.

13 Claims, No Drawings

DRUG OR DERMATOLOGICAL COMPOSITION CONTAINING AN AVOCADO PEPTIDE EXTRACT FOR TREATING AND PREVENTING PRURITUS

The present invention relates to a drug or dermatological composition containing an avocado peptide extract for treating pruritus and non-infectious disorders involving itching.

The use of avocado peptide extracts in the treatment or prevention of diseases related to a deficiency of the immune system have already been described in the patent application WO2005/105123. Indeed, it has been shown that avocado peptide extracts are able to increase the production of antimicrobial peptides, in particular human β-defensin-2 (hBD-2). Such extracts are thus particularly suited for treating or preventing inflamed or immature skin or the skin of immunosuppressed individuals. It also has been shown that such avocado peptide extracts do not induce inflammatory reactions, irritations or intolerances.

In addition to this action on inflamed or immature skin or the skin of immunosuppressed individuals, the Inventors have now discovered, in a surprising way, that a composition containing an avocado peptide extract can be used to treat or prevent pruritus and noninfectious disorders involving itching.

Pruritus is a functional sign and is defined as "a sensation that causes the desire to scratch." It can be localized, diffuse or generalized. It is particular at the skin and the semi-mucosa. Scratching makes pruritus disappear completely, but only temporarily. Repetitive, intense scratching can lead to cutaneous lesions. In the context of the present invention, the term "pruritus" refers to pathological pruritus which is a nuisance for the patient, sometimes even disabling. It can be sufficiently unpleasant to make the patient prefer pain to itching, which can explain the lesions induced by scratching.

The cutaneous sensation commonly referred to as itching can be regarded as a uniform response to a wide variety of endogenous or exogenous physical and chemical stimuli. These stimuli act on the receptors of free nerve endings located at the dermal-epidermal junction and around hair follicles. The principal agent responsible for itching is histamine, a chemical molecule released in particular by mast cells. Histamine, when released, binds to skin nerve receptors and causes pruritus. The sensation is transmitted by the same nerve fibers that transmit the sensations of pain to the brain.

Like histamine, tryptase, a protease also released by mast cells, is also heavily involved in the physiopathology of pruritus: tryptase induces the pruritus signal by binding to protease receptors (protease-activated receptor-2, or PAR-2) on nerve fibers.

Pain, temperature and touch are all sensations transmitted by the same unmyelinated free nerve fibers innervating human skin. Low-intensity simulation of these fibers will cause pruritus, while more intense stimulation will lead to a genuine sensation of pain. Although they are transmitted via the same sensory fibers, the neural impulses of itching have a much lower frequency than impulses of pain; however, if scratching follows in response to the itching stimulus, nerve impulse frequency increases with scratching intensity and the corresponding sensation changes from itching to pain.

Itching can be induced by a wide variety of circumstances, both physiological and pathological. In particular, when it is generalized and associated with cutaneous lesions such as blisters and papules, itching is often the effect of a primary dermatological disease; in many cases, it is the fundamental diagnosis symptom. On the other hand, in the absence of cutaneous lesions (on healthy skin), itching can arise in many cases from systemic disorders such as, for example, neoplastic diseases, metabolic disorders, also allergic reactions or hypersensitivity to certain drugs, or pregnancy. Lastly, in other cases, itching appears to be the only dominating chronic symptom, without the possibility of any clarification of the etiopathogenesis of this ailment. In these cases, itching is normally indicated by pruritus sine materia, i.e., it represents a symptom of unknown origin which is not classifiable in the absence of identifiable extracutaneous or cutaneous changes. The only objective signs, although secondary, of the disorder concerned are limited to scratch marks such as linear excoriations and, if the situation lasts for a longer period of time, small secondary papules (i.e., papules due to scratching) and signs of lichenification with hyperpigmentation in the most chronic cases.

The present invention relates to a drug or dermatological composition containing an avocado peptide extract, which contains 2% to 10% by weight of alpha-amino nitrogen in relation to the weight of dry matter of the peptide extract, and a suitable excipient, for the use of same for treating or preventing internal pruritus and noninfectious disorders involving itching.

Non-infectious disorders involving itching refer to unexplained itching which is not due to infections.

Pruritus can be subdivided into two types: localized pruritus (such as insect bites, seborrheic dermatitis, tinea, candidiasis) and diffuse pruritus.

The invention relates to diffuse pruritus.

Said diffuse pruritus can be subdivided into two families: the presence of specific cutaneous lesions is characteristic of pruriginous dermatosis; the absence of specific cutaneous lesions (except for possible lesions from scratching) is characteristic of internal pruritus.

The invention relates to the treatment and prevention of internal pruritus. Said internal pruritus is not the result of any inflammatory dermatosis or a deficiency of the immune system (in particular of innate immunity).

Thus, the present invention relates to the treatment and prevention of pruritus associated with various forms of itching whose etiology is not in connection with dermatological lesions, in particular allergic lesions (eczema, urticaria, atopic dermatitis, irritant or contact dermatitis, polymorphic light eruption, drug eruption, allergic reaction) or infectious lesions (cutaneous parasitosis, dermatophytosis, phthiriasis of the body and scalp, varicella, HIV, lepidopterism). In particular, the expression "internal pruritus" does not include irritant dermatitis.

The pruritus is advantageously selected from the group comprising pruritus gravidarum, pruritus sine materia, neonatal pruritus (related to xerosis) and drug-related pruritus. The invention thus relates to a drug containing an avocado peptide extract, which contains 2% to 10% by weight of alpha-amino nitrogen in relation to the weight of dry matter of the peptide extract, and a suitable excipient, to treat or prevent a pruritus selected from the group comprising pruritus gravidarum, pruritus sine materia, neonatal pruritus (related to xerosis) and drug-related pruritus.

According to an advantageous variation of the invention, the drug or dermatological composition, which contains the avocado peptide extract and at least one excipient, is for treating and preventing pruritus gravidarum.

Ten to twenty percent of pregnancies are complicated by pruritus gravidarum, which in pregnant women is a diffuse pruritus without specific cutaneous lesions of an inflammatory or allergic dermatosis.

A particular example of pruritus gravidarum is obstetric cholestasis. This "third-trimester cholestasis" is the leading cause of jaundice during pregnancy. Estrogens and progesterone appear to play an essential role in this pruritus. An isolated and intense pruritus bringing about insomnia and lesions from scratching is the first symptom of obstetric cholestasis. Jaundice can also be present.

The avocado peptide extract according to the invention is also active in the treatment of prurigo gravidarum, which would be secondary to obstetric cholestasis and whose outward signs are an eruption of small pruriginous papules.

According to an advantageous variation of the invention, the drug or dermatological composition, which contains the avocado peptide extract and at least one excipient, is for treating and preventing pruritus sine materia.

The pruritus sine materia group includes symptoms of itching appearing with no connection to organic lesions or to systemic or skin diseases (thus referred to as psychogenic pruritus) in the external genital regions (such as pruritus vulvae and pruritus scroti) and in the perianal region (pruritus ani) as well as pruritus of aged skin (senile pruritus).

Psychogenic pruritus (itching of psychological origin) is a relatively frequent pruritus.

Psychogenic pruritus covers:
 parasitophobia in which patients, over 40 years of age, believing themselves to be infested by parasites, proceed with repeated and mutilating digging of the skin;
 factitious disorder which accounts for all the lesions caused or aggravated by the various actions of the patient, principally digging with the nails.

Senile pruritus is a generalized affection, widespread among persons aged 65 and older. It is known to have a psychogenic component. Senile pruritus is aggravated by desiccation of the skin and cutaneous dryness. Dehydrated skin, generally combined with exposure to ambient conditions of low moisture and temperature, induces fine cracking and desquamation of the skin of elderly subjects, with persistent and diffuse itching as a consequence.

According to an advantageous variation of the invention, the drug or dermatological composition, which contains the avocado peptide extract and at least one excipient, is for treating and preventing neonatal pruritus related to neonatal xerosis.

The skin structure of a full-term neonate is identical to that of an infant. However, the skin of a full-term neonate has the distinctive characteristic of physiological desquamation. The latter affects 65% of full-term neonates and is the most significant neonatal cutaneous change. It indicates the existence of significant cutaneous xerosis. It is more marked on the hands, ankles and feet, but it can be more widespread. Such desquamation disappears spontaneously during the first two weeks of life.

The Inventors have noted with interest that the avocado peptide extract according to the invention makes it possible to prevent or treat said xerosis in full-term neonates, in particular to quickly control (before the desquamation disappears naturally) the desquamation observed. The avocado peptide extract according to the invention also enables hydration and/or refatting of the skin of neonates and thus accelerates the disappearance of the desquamation observed.

According to an advantageous variation of the invention, the drug or dermatological composition, which contains the avocado peptide extract and at least one excipient, is for treating and preventing drug-related pruritus.

Drug-related pruritus is due to the continuous or intermittent use of certain drugs (barbiturates, antibiotics, aspirin, sulfonamides, etc.).

Examples of molecules likely to cause the appearance of pruritus include acetylsalicylic acid, antimalarials (chloroquine), antiretrovirals (protease inhibitors), angiotensin-converting enzyme (ACE) inhibitors, interferon, opiates (heroin), phenothiazines, retinoids, tolbutamide and finally group B vitamins. The application on the skin of irritating substances for cosmetic use (e.g., exfoliants) or professional use (e.g., glass wool) can also cause pruritus, whether said pruritus is or is not associated with cutaneous lesions.

During intense and chronic pruritus, lichenification of the skin, which is a particular form of cutaneous thickening, can also appear. When lichenification lesions take on a nodular appearance, they indicate prurigo. In addition, these lichenification lesions are themselves pruriginous and as a result contribute to the maintenance of pruritus. The avocado peptide extract according to the invention is also suitable for preventing or treating such lichenification.

Quite interestingly, the Inventors have noted that, in addition to its effect on the prevention or treatment of pruritus, the avocado peptide extract also has a refatting or hydrating activity, which strengthens its action on pruritus, in particular senile pruritus or neonatal pruritus. The invention thus further relates to a drug or dermatological composition as previously described, characterized in that it has in addition a hydrating and refatting activity.

The drug or dermatological composition according to the invention is particularly suited for treating internal pruritus, which can be associated with cutaneous dryness or desquamation, in pregnant women, full-term neonates and the elderly. Advantageously, the drug or dermatological composition is indicated for pregnant women or full-term neonates.

In the context of the present invention, the expression "alpha-amino nitrogen" refers to the nitrogen content of peptides in the form of free alpha-amino groups. Measuring the alpha-amino nitrogen content of peptides makes it possible to evaluate the degree of hydrolysis of proteins as well as the average molar mass of the peptides.

The avocado peptide extract can be obtained directly from any part of the avocado or avocado tree, such as the fruit, skin or pit of the avocado or the leaves or roots of the avocado tree. It is also possible to obtain the avocado peptide extract from the by-products of the avocado processing industry, including but in no way exhaustively: fresh avocado pulp, frozen pulp, dehydrated pulp, avocado oil cakes arising from oil extraction processes (mechanical extraction and/or extraction by solvent using fruit dehydrated beforehand), de-oiled solid matter arising from wet oil extraction processes (so-called centrifugation processes), de-oiled solid matter arising from enzymatic avocado oil extraction processes, crude mashed avocado (guacamole) and solid waste from units that manufacture such mashed avocado. The extract is advantageously obtained from the fresh fruit of the avocado tree. The fruits can be selected among the Hass, Fuerte, Ettinger, Bacon, Nabal, Anaheim, Lula, Reed, Zutano, Queen, Criola Selva, Mexicana Canta, Region Dschang, Hall, Booth, Peterson, and Collinson Red varieties, more advantageously among the Hass, Fuerte and Reed varieties. Preferably, the Hass, Fuerte, Ettinger and Bacon varieties will be selected, and more advantageously the Hass and Fuerte varieties.

The fruit of the avocado tree is primarily composed of water, pulp, oil and pit. The proportions of these components are, like all natural and plant matter, highly variable. However, the mean composition data presented in table 1 below, expressed in percentages of fresh fruit, are generally accepted:

TABLE 1

| | |
|---|---|
| Water | 70%-85% |
| Proteins | 1.5%-4.5% |
| Fats | 12%-23% |
| Sugars | 1.5%-5% |
| Fibers | 1.1%-1.6% |

In relation to the pulp, avocado proteins represent 1.5% to 2.5% (J. P. Gaillard, L'Avocatier, Edition G. P. Maisonneuve et Larose, 1987, pp. 266-67). The distribution of amino acids, expressed in weight percentage in relation to the total weight of the amino acids, is presented in following table 2:

TABLE 2

| | |
|---|---|
| Alanine | 5-7 |
| Arginine | 3-5 |
| Aspartic acid | 8-12 |
| Cystine-cysteine | <1 |
| Glutamic acid | 11-13 |
| Glycine | 4-6 |
| Histidine | 4-6 |
| Isoleucine | 4-7 |
| Leucine | 8-11 |
| Lysine | 4-7 |
| Methionine | 1-3 |
| Phenylalanine | 4-6 |
| Proline | 4-7 |
| Serine | 4-6 |
| Threonine | 4-6 |
| Tyrosine | 3-6 |
| Valine | 4-7 |

The principal amino acids are glutamic acid, aspartic acid and leucine.

As compared with classic oil and protein producing crops such as soy, sunflower or rapeseed, the avocado is distinctly lower in protein content. Moreover, the avocado's relatively high fiber content makes these proteins highly difficult to access via classic chemical or biochemical pathways. Additionally, the very little hydrosoluble character of these natural macromolecules suggests preparing hydrolyzed fractions of these proteins (peptides), showing very high water-solubility and much better bioavailability. In this way, their allergenic potential may also be eliminated. The invention thus also relates to the preparation of an avocado peptide extract via a controlled synthesis pathway which does not denature hydrolyzed proteins The avocado peptide extract is advantageously a delipidated aqueous extract. Said delipidated aqueous extract advantageously undergoes enzymatic hydrolysis. The avocado proteins were advantageously hydrolyzed by proteases. According to an advantageous variation of the invention, the sugars present in the delipidated aqueous extract are also hydrolyzed (in the presence of glucanases, for example).

More particularly, the avocado peptide extract may be obtained by a method comprising the following steps:
an avocado oil cake is obtained, advantageously from avocado fruit, through drying and extraction of the oil (lipids); after which
said oil cake is cold crushed (cryogrinding) and totally delipidated, then decanted, centrifuged and collected; after which
a first hydrolysis is carried out in the presence of glucanases, followed by centrifugation and the elimination of the soluble fraction;
a second hydrolysis is carried out in the presence of one or more proteases, followed by centrifugation and the elimination of the pellet; after which
the peptide phase is concentrated by nanofiltration;
decolorizing is carried out in the presence of activated carbon, for example, followed by simple filtration (10 µm), then by ultrafiltration (10 kDa cutoff); and finally
if need be, final sterilizing microfiltration (0.2 µm), adding of preservative and packaging.

According to an advantageous variation of the invention, the first step of the method consists in drying, then deoiling the fruit. Thus, after the fruit has been cut into thin slices, it may be dried by any of the techniques known to those persons skilled in the art, among which may be cited hot air drying, lyophilization or osmotic drying. In general, the temperature during this drying step will be advantageously maintained at or below 80° C., regardless of the technique used. In the context of the present method, for reasons of easy implementation and cost, drying in ventilated dryers, in thin layer and under a stream of hot air at a temperature between 70° C. and 75° C., is preferred. The duration of this operation may vary between 5 hours and 72 hours.

The lipids of the dried fruit are then extracted either mechanically in an expeller, or chemically with a solvent such as hexane in a Soxhlet extractor or in a De Smet® continuous belt extractor, notably according to the method described in French application FR 2843027, or by a method using supercritical $CO_2$. Among the main advantages of the method, the oil by-product can quite clearly be recovered directly. For this reason mechanical lipid extraction is preferred.

The dried and deoiled fruit, also called an oil cake, may then undergo the following steps:
cryogrinding,
total delipidation, notably with a nontoxic food grade solvent such as ethanol and/or acetone,
decanting and washing of the oil cake with water,
centrifugation and collection of the oil cake,
a first hydrolysis in the presence of one or more glucanases,
centrifugation and discarding of the soluble fraction,
a second hydrolysis in the presence of one or more proteases,
centrifugation and discarding of the pellet,
concentration through nanofiltration,
decolorization in the presence of activated carbon,
simple filtration (10 µm) followed by ultrafiltration (10 kDa cutoff),
adding of a preservative, final sterilizing microfiltration (0.2 µm) and packaging.

The final aqueous extract may contain 1% to 60% dry matter by weight, or 3% to 20% dry matter by weight, preferably 5% to 6% dry matter by weight. In relation to the weight of dry matter, the weight content in alpha-amino nitrogen may be between 2% and 10%, preferably between 5% and 7%. The pH value of a 1.2% by weight of dry extract aqueous solution will generally be between 3 and 6, more advantageously between 4 and 5. Mean analytic data for a 1.2% by weight of dry extract aqueous solution, as obtained by the method described above, are presented in the following table 3:

TABLE 3

| | | |
|---|---|---|
| α-Amino nitrogen (o-phthalaldehyde or ninhydrin method) (in weight percentage of dry matter) | | 4-10 |
| Proteins (in weight percentage of dry matter) (N × 6.25)[1] | | 10-30 |
| pH (¼ dilution) | | 4.5-7.0 |
| Absorbance (¼ dilution) | 420 nm | 0.1-0.6 |
| | 550 nm | 0.02-0.1 |

[1]N × 6.25 is the total nitrogen content (N) of a sample multiplied by a specific coefficient for the assayed protein. When the coefficient for the assayed proteins is not known with precision, a coefficient of 6.25 is used by convention.

The following table 4 presents the mean amino acid composition of the peptide extract as obtained by the method according to the invention, wherein the values are expressed in weight percentage in relation to the total weight of the amino acids assayed. Values for aspartic acid and glutamic acid also include asparagine and glutamine contents, respectively.

TABLE 4

| Amino acid | Minimum value | Maximum value |
| --- | --- | --- |
| Alanine | 6.4 | 7.8 |
| Arginine | 4.7 | 5.7 |
| Aspartic acid | 10.3 | 12.7 |
| Cystine-cysteine | 2.9 | 3.5 |
| Glutamic acid | 13.0 | 15.8 |
| Glycine | 5.3 | 6.5 |
| Histidine | 2.2 | 2.6 |
| Isoleucine | 4.8 | 5.8 |
| Leucine | 7.6 | 9.4 |
| Lysine | 3.0 | 3.8 |
| Methionine | 1.2 | 1.6 |
| Phenylalanine | 4.7 | 5.7 |
| Proline | 4.1 | 5.2 |
| Serine | 5.5 | 6.7 |
| Threonine | 4.6 | 5.6 |
| Tyrosine | 3.6 | 4.4 |
| Valine | 5.8 | 7.2 |

Tryptophan not assayed.

The extract obtained may be lyophilized in order to obtain a solid powder (dry extract), but it is totally hydrosoluble in comparison to the original avocado proteins.

According to an advantageous variation of the invention, at least 50% of the extract peptides are comprised of 10 to 30 amino acid motifs. These peptides are therefore much smaller compared with native avocado proteins. As such, these peptides thus have much better bioavailability, notably cutaneous bioavailability.

According to an advantageous variation of the invention, the drug or dermatological composition comprises 0.01% to 20% in dry weight of the avocado peptide extract, in relation to the total weight of said drug or dermatological composition, even more advantageously 0.1% to 15% in dry weight of the avocado peptide extract, even more advantageously 0.5% to 10% in dry weight of the avocado peptide extract, even more advantageously 0.7% to 8% in dry weight of the avocado peptide extract, and even more advantageously 1% to 5% in dry weight of the avocado peptide extract.

The drug or dermatological composition according to the invention can further comprise at least one compound selected from the group comprising anti-irritant and/or soothing and/or cicatrizing and/or anti-aging and/or hydrating agents.

The anti-irritant and/or soothing and/or cicatrizing and/or anti-aging and/or hydrating agents which can be used in the context of the present invention in combination with the avocado peptide extract are advantageously glycine, plant sugars and/or peptides including lupine, lupeol (FR 2822821, FR 2857596), oxazolines (WO 03/055463), oxazolidinones (WO 2004/050052), lipoic acid, alpha bisabolol, licorice derivatives, enoxolone, ectoine, avocado furans (in particular Avocadofurane®: avocado furans, which can be obtained by the method described in international application WO 01/21605), Centella asiatica extracts, in particular madecassic acid or asiatic acid, caffeine, retinol, retinal, retinoic acid, zinc oxide, magnesium, silicon, copper, zinc, manganese, selenium, hyaluronic acid, azelaic acid and salts or esters thereof, salicylic acid and derivatives thereof, alpha hydroxy acid (AHA), AHA esters, pyrrolidone carboxylic acid and derivatives thereof, cholesterol, squalane, phospholipids, beta carotene, vitamin A, vitamin E, vitamin C, vitamin B3 (niacinamide, nicotinamide), vitamin B5 (panthenol), vitamin B6, benzoyl peroxide, urea, coenzyme Q10, glucosamine and salts thereof, N-acetyl glucosamine, thermal or spring waters (Avène, Roche Posay, Saint Gervais, Uriage, Gamarde), soy peptides and arabinogalactan (in particular arabinogalactan can be combined with lupeol or soy peptides).

The oxazolines which can be used in the context of the present invention in combination with the avocado peptide extract are advantageously oxazolines selected from the group comprising 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. In an even more advantageous way, said oxazoline is 2-undecyl-4,4-dimethyl-1,3-oxazoline, called OX-100 or Cycloceramide®.

In addition to said active agents, the avocado peptide extract according to the invention, alone or in combination with the active agents cited above, can be used in combination with active agents providing protection from the sun, such as UVB and/or UVA sun screens or filters; such mineral and/or organic screens or filters are known to those persons skilled in the art who will adapt the choice and concentrations of said screens or filters according to the degree of protection sought.

Examples of active agents that provide protection from the sun include in particular titanium oxide, zinc oxide, methylene bis-benzotriazolyl tetramethylbutylphenol (brand name: Tinosorb M) and bis-ethylhexyloxyphenol methoxyphenyl triazine (brand name: Tinosorb S).

In addition to these active agents, the avocado peptide extract according to the invention, alone or in combination with the active agents cited above, can be used in combination with avocado sugars, cutaneous barrier restructuring agents, antifungal compounds, antiseptic preservatives and compounds containing vegetable oil unsaponifiables, lupine peptides, avocado oil, butyl avocadate, cycloceramides, genistein, colza concentrates or corn concentrates.

The avocado sugars are advantageously D-mannoheptulose and/or perseitol. The avocado sugars are more advantageously the hydrosoluble extract of avocado sugars described in application WO 2005/115421.

The cutaneous barrier restructuring agents, which stimulate the synthesis of the key lipids of the epidermis, which can be used in the context of the present invention in combination with the avocado peptide extract are advantageously sunflower concentrates, even more advantageously linoleic sunflower concentrates such as the active agent marketed by Laboratoires Expanscience, Soline® (see international application WO 01/21150), vegetable oil unsaponifiables such as Avocadofurane® (see international application WO 01/21150) or PPAR agonists (rosiglitazone, pioglitazone).

The antifungal compounds which can be used in the context of the present invention in combination with the avocado peptide extract are advantageously econazole and ketoconazole.

The antiseptic preservatives which can be used in the context of the present invention in combination with the avocado peptide extract are, for example, triclosan, chlorhexidine or quaternary ammoniums.

The compounds containing vegetable oil unsaponifiables which can be used in the context of the present invention in combination with the avocado peptide extract are advantageously selected from the group comprising furanic lipids of avocado, avocado unsaponifiables, soy unsaponifiables, avocado and soy unsaponifiables, lupine oil concentrates, sunflower oil concentrates and mixtures thereof.

The furanic lipids of avocado which can be used in the context of the present invention in combination with the avocado peptide extract are advantageously natural 2-alkyl furans, in particular the active agent Avocadofurane® marketed by Laboratoires Expanscience, which can be obtained by the method described in international application WO 01/21605.

The avocado and soy unsaponifiables which can be used in the context of the present invention in combination with the avocado peptide extract are advantageously a mixture of furanic unsaponifiables of avocado and unsaponifiables of soy in a ratio of roughly 1:3 to 2:3, respectively. The avocado and soy unsaponifiables are even more advantageously the product Piascledine®, marketed by Laboratoires Expanscience.

The lupine oil concentrates which can be used in the context of the present invention in combination with the avocado peptide extract are advantageously concentrates obtained by molecular distillation of lupine oil, advantageously sweet white lupine oil, such as those described in international application WO 98/47479. They advantageously contain approximately 60% unsaponifiables by weight.

The sunflower oil concentrates which can be used in the context of the present invention in combination with the avocado peptide extract are advantageously linoleic sunflower concentrates, such as the active agent marketed by Laboratoires Expanscience, Soline® (see international application WO 01/21150).

The drug or dermatological composition according to the invention can be formulated in the form of various preparations suitable for topical administration. Preferably the various preparations include creams, milks, lotions, waters, oils, patches, sprays or any other product for external application.

The optimal modes of administration, dosing schedules and dosage forms of the compounds and compositions according to the invention can be determined according to criteria generally taken into account in establishing a pharmaceutical treatment, in particular a dermatological treatment, adapted to a patient to include, for example, the patient's age or weight, general condition, tolerance of the treatment, side effects observed and skin type. The patient is advantageously a pregnant woman, a full-term neonate or elderly, more advantageously a pregnant woman or a full-term neonate.

According to the type of administration desired, the drug and/or active compounds according to the invention can further comprise at least one pharmaceutically acceptable excipient, in particular at least one dermatologically acceptable excipient. Preferably, an excipient suited for external topical application is used. The drug or dermatological composition according to the present invention can further comprise at least one pharmaceutical adjuvant known to those persons skilled in the art selected from thickeners, preservatives, fragrances, colorants, chemical or mineral filters, hydrating agents, thermal spring waters, etc.

Considering the patients concerned, in particular pregnant women and full-term neonates, the drug or dermatological composition will not comprise excipients with notorious effects, such as allergens, soaps containing iodine, benzyl alcohol, penetration vectors (glycol) and compounds that are category 1, 2 or 3 carcinogens, mutagens or reproductive toxins. Moreover, the fragrances optionally contained in the formulation will be advantageously neutral fragrances.

The following examples illustrate the invention without limiting the scope of the invention in any way.

EXAMPLE 1

Preparation of an Avocado Peptide Extract

Fifty kilograms of fresh avocados, the Hass variety, are cut into thin slices 2-5 mm thick, pit included, using a slicer with a circular blade. The drying apparatus is a temperature controlled hot air flow drying oven. The sliced avocados are distributed in a thickness of 4-5 cm on stacked racks. Drying is for 48 hours at a temperature of 80° C. Once dried, the fruits are subjected to cold pressing. This operation is carried out on a small Komet® laboratory press.

Four kilograms of delipidated fruits (oil cake) are cold crushed and then extracted at reflux in the presence of 25 liters of ethanol. The fat-depleted powder is then recovered by filtration on a Buchner funnel and oven dried at 50° C. for 5 hours.

The oil cake is washed with demineralized water (10 liters) and then separated by centrifugation. The solid fraction is taken up in an aqueous solution, acidified by HCl (pH 5) and then mixed with cellulase (2% in relation to the dry matter). The duration of hydrolysis is 6 hours.

The mixture is then centrifuged at 2000 g in the presence of adjuvant (2.5% w/v). The recovered pellet then undergoes a second hydrolysis at pH 8.0, in the presence of 0.5% protease, at a temperature of 55° C. for 2 hours. Hydrolysis is maintained at constant pH by continuously adding 2 M soda. The protease is finally denatured by heating for 10 minutes at 85° C.

The mixture obtained is centrifuged and the supernatant filtered by passing through a 7.5 μm membrane. It is then ultrafiltered on 10 kDa-cutoff membranes.

The crude peptide extract obtained (20% dry matter) is decolorized in the presence of 1% activated carbon and then filtered again through a 7.5 μm membrane. The decolorized extract is then microfiltered (0.2 μm), titrated to 5% dry matter (DM), supplemented with preservative and finally packaged after sterilizing filtration (0.2 μm).

The characteristics of the hydrosoluble avocado peptide extract (5% DM) obtained by the present method are given in the following table 5:

TABLE 5

| Appearance | Slightly orange solution |
|---|---|
| Analytical criteria | |
| Dry matter | 5% |
| pH (¼ dilution) | 4.5 |
| Absorbance at 420 mm (¼ dilution) | 0.152 |
| Absorbance at 550 mm (¼ dilution) | 0.035 |
| Composition of the dry matter | |
| Alpha-amino nitrogen | 6.7% |
| Proteins | Not detected |
| Preservative | 0.4% |

The following table 6 presents the distribution of molecular masses in the avocado peptide extract obtained by the present method:

TABLE 6

| HPLC peak | Molar mass (g/mol) | Mean number of amino acids | Relative % |
|---|---|---|---|
| 1 | >3480* | <29 | 1% |
| 2 | 3480 to 1180 | 29 to 9 | 26% |

TABLE 6-continued

| HPLC peak | Molar mass (g/mol) | Mean number of amino acids | Relative % |
|---|---|---|---|
| 3 | 1180 to 310 | 9 to 2 | 45% |
| 4 | 310 to 130 | 2 to 1 | 15% |
| 5 | <130 | 1 | 13% |

*Masses < 10,000 g/mol.

It should be noted that at least 27% of the peptides of the extract consist of at least 9 amino acid motifs. Consequently, the size of the peptides of the extract is thus extremely small in comparison to that of native avocado proteins. These peptides thus have a much better bioavailability, in particular cutaneous bioavailability.

EXAMPLE 2

Activities of the Avocado Peptide Extract on Pruritus

Pruritus is defined as an unpleasant cutaneous sensation which provokes the desire to scratch. The pruritus "message" is transmitted by the free endings of C fibers.

The mast cell seems to play a fundamental role in pruritus of cutaneous origin. Indeed, many pruriginous substances cause its degranulation. During its degranulation, the mast cell excretes various products, including:
  histamine, whose release causes the activation of H1 receptors on nerve fibers and thus induction of the pruritus signal,
  proteases, in particular tryptase, which induce the pruritus signal by binding to protease receptors (protease-activated receptor-2, or PAR-2) on nerve fibers.

The release of pruriginous mediators by the mast cell, which leads to the transmission of the pruritus nerve signal, also has other consequences which amplify the phenomenon:
  thus, the activation of PAR-2 on nerve fibers by tryptase causes these fibers to release neuropeptides such as substance P and calcitonin gene-related peptide (CGRP). Substance P is in turn able to induce mast cell degranulation. CGRP and substance P also act on the endothelial cells, therefore inducing vasodilatation, extravasation and thus inflammatory cell recruitment;
  histamine is also able to stimulate the release by sensory nerves of neurotransmitters such as substance P and neurokinin A, which can lead to mast cell degranulation (and thus amplification of the reaction);
  tryptase can also activate and induce degranulation of the mast cell, which also has PAR-2;
  similarly, endothelial cells can respond to tryptase stimulation via PAR-2;
  in addition, endothelial cells can also respond to histamine stimulation;
  lastly, PAR-2 is also expressed by epidermal keratinocytes in which it is involved in an inflammatory reaction via the activation of the NFκB transcription factor.

The studies presented below were carried out on rat peritoneal mast cells. These cells have the same features as cutaneous mast cells and thus constitute an experimental model representative of human skin.

I. Effect of the Avocado Peptide Extract on the Release of Tryptase by Mast Cells
  I.1. Materials and Methods:
  Rat peritoneal mast cells ($2\times10^3$ cells/ml) were incubated for 30 minutes at 37° C. in the presence or absence of 0.005% (w/v) avocado peptide extract (obtained in example 1) or 50 μM quercetin (Sigma), the reference tryptase release inhibitor. The cells were then stimulated for 15 minutes by 0.5 μM calcium ionophore A23187 (Millipore). The calcium ionophore is used to induce the release of tryptase (it induces an influx and mobilization of intracellular calcium). The reaction was quenched by centrifugation at 4° C.

Tryptase release was evaluated by assaying tryptase in the cell pellets and supernatants by means of the Mast Cell Degranulation Assay Kit (Millipore). This test is based on the spectrophotometric detection of the chromophore p-nitroaniline (pNA) after cleavage of the tosyl-gly-pro-lys-pNA substrate by tryptase.

The absence of cytotoxicity of the avocado peptide extract under the test conditions was confirmed by staining with trypan blue.

I.2. Results:

As shown in table 7, the calcium ionophore A23187 induced a massive release of tryptase and 50 μM quercetin significantly inhibited this release (−47%, p<0.01); these conditions validate the test.

TABLE 7

Release of tryptase by mast cells

| | Tryptase (ng/ml) | | |
|---|---|---|---|
| | Mean | Standard deviation | Percentage inhibition |
| Non-stimulated control | 2 | 1 | |
| Stimulated control (Ca ionophore) | 83 | 5 | |
| 50 μM quercetin | 44 | 2 | −47%** |
| 0.005% avocado peptide extract | 58 | 7 | −30%** |

**p < 0.01: Student's t-test

The avocado peptide extract at a concentration of 0.005% (w/v) significantly inhibited (−30%) the release of tryptase by mast cells induced by the calcium ionophore.

II. Effect of the Avocado Peptide Extract on the Release of Histamine by Mast Cells
  II.1. Materials and Methods:
  Rat peritoneal mast cells (10,000 cells in suspension/250 μl Tyrode's buffer) were incubated for minutes at 37° C. in the presence or absence of 0.05%, 0.5% and 1% (w/v) avocado peptide extract, obtained in example 1, or 10 mM calcium, used as the reference histamine release inhibitor.

The cells were then stimulated for 10 minutes by 10 μM substance P (Neosystem) in the presence of 0.3 mM calcium.

The reaction was quenched by centrifugation and the supernatants and cell pellets were taken up in 0.8 N perchloric acid in order to assay histamine using the spectrofluorometric method.

The quantities of histamine released were expressed as a percentage of release (quantity in supernatants/total quantity).

The absence of cytotoxicity of the avocado peptide extract under the test conditions was confirmed by a lactate dehydrogenase (LDH) assay.

II.2. Results:

As shown in table 8, histamine release was strongly stimulated by substance P, and 10 mM calcium significantly inhibited (−78%) this release; these conditions validate the test.

TABLE 8

Release of histamine by mast cells

| | Histamine (% release) | | |
|---|---|---|---|
| | Mean | Standard deviation | Percentage inhibition |
| Non-stimulated control | 2 | 1 | |
| Stimulated control (substance P) | 74 | 5 | |
| 10 µM calcium | 16 | 1 | −78%** |
| 0.05% avocado peptide extract | 58 | 5 | −21%* |
| 0.5% avocado peptide extract | 60 | 4 | −19%* |
| 1% avocado peptide extract | 35 | 2 | −53%** |

*$p < 0.05$;
**$p < 0.01$: Student's t-test

The avocado peptide extract at concentrations of 0.05%, 0.5% and 1% (w/v) led to a significant and dose-dependent inhibition of histamine release induced by substance P (−21%, −19% and −53%, respectively).

III. Effect of the Avocado Peptide Extract on Gene Expression of PAR-2 in Reconstructed Epidermis III.1. Materials and Methods:

Seventeen-day reconstructed epidermises (Skinethic) were treated systemically with 0.04% (w/v) avocado peptide extract (obtained in example 1) or 1 µM retinoic acid (Sigma, positive reference) for 6 hours.

Gene expression was analyzed using standard simplified DNA arrays. These microarrays involved spotting specific cDNA markers of interest on nylon membranes. Analysis was carried out according to a suitable miniaturized and optimized technology based on the use of messenger RNA and $^{33}$P labeling.

When culturing was complete, the epidermises were rinsed with phosphate buffered saline (PBS) solution. The total RNA of the epidermises was then extracted and purified using TRI Reagent (Sigma) according to a standardized protocol. RNA quantity and quality were then evaluated using an Agilent 2100 bioanalyzer. The mRNA of each culture was reverse transcribed using oligo(dT) and a $^{33}$P-labeled deoxyribonucleotide triphosphate. Multiple labeled cDNA "target" sequences were prepared for each culture. These targets were then hybridized, under optimized conditions, with cDNA "probes" in excess bound to membranes. After washing, the relative quantity of labeled target was measured by direct counting using a Phosphorlmager.

The membranes were analyzed using suitable software. The resulting data demonstrate the differential expression of various genes following treatment with the avocado peptide extract in comparison to the corresponding control.

III.2. Results:

As shown in table 9, PAR-2 gene expression in reconstructed epidermises was inhibited (−29%) by retinoic acid, the test control.

TABLE 9

PAR-2 gene expression in reconstructed epidermises
PAR-2 (relative expression)

| | Mean | Standard deviation | Percentage inhibition |
|---|---|---|---|
| Control epidermises | 4.2 | 0.1 | |
| 1 µM retinoic acid | 3 | 0.3 | −29% |
| 0.04% avocado peptide extract | 2 | 0 | −52% |

The avocado peptide extract, at a concentration of 0.04% (w/v), induced inhibition of PAR-2 gene expression (−52%).

IV. Conclusion

It was shown that the avocado peptide extract is able to modulate the release of histamine and tryptase by mast cells. Thus, the avocado peptide extract has an inhibiting effect on the mast cell degranulation at the origin of the induction and maintenance of the pruritus reaction. In addition, an inhibiting effect of the avocado peptide extract on epidermal expression of PAR-2 (protease-activated receptor-2) was shown.

The peptide extract can thus prevent the effects of PAR-2 activation in the development of pruritus; more particularly, the avocado peptide extract can modulate the effects of tryptase on its various cell targets since tryptase is an endogenous PAR-2 agonist.

EXAMPLE 3

Hydrating and Refatting Activities of the Avocado Peptide Extract

The natural hydration of the skin is principally due to its content in glycosaminoglycans (GAGs), in particular hyaluronic acid.

Glycosaminoglycans other than hyaluronic acid are molecules composed of a peptide portion and a carbohydrate portion. They are heavily involved in the retention of water in the dermis and thus contribute to the maintenance of a suitable level of hydration.

Hyaluronic acid (HA) is composed exclusively of carbohydrate molecules. It is notably an important factor in the thickening of the skin: by strongly binding with water, it forms a dense viscoelastic network and thus contributes to skin density, cohesion, hydration and elasticity. With age, there is a decrease in HA content in the skin.

The synthesis of sulfated GAGs and HA was studied on keratinocytes in culture following treatment with the avocado peptide extract, according to example 1, in order to evaluate its hydrating activity.

One of the principal functions of the skin is that of protective barrier against environmental stresses and water loss.

The permeable barrier of the skin is located in the outermost layer of the skin, the stratum corneum. Corneocytes (keratinocytes in an advanced state of differentiation), the constitutive cells of the stratum corneum, are enclosed in a lipid-rich extracellular matrix. It is this lipid-rich matrix which is at the origin of the permeable barrier function.

The lipids of the stratum corneum are principally composed of ceramides (50% of the total mass of the lipids), cholesterol (25%) and free fatty acids (10%).

The content in these three key lipids of the stratum corneum is reduced in the case of xerosis; this decrease would come from a drop in enzymatic activity which limits the synthetic pathways of these lipids.

The effect of the avocado peptide extract on the neosynthesis of epidermal lipids was evaluated in a model of reconstructed skin, with a separate analysis of phospholipids (cell membranes) and neutral lipids (including the "special" lipids of the skin).

I. Effect on the Synthesis of Glycosaminoglycans and Hyaluronic Acid by Keratinocytes (Hydrating Activity)

I.1. Materials and Methods:

Normal human epidermal keratinocytes (NHEK) were pre-cultured for 24 hours at 37° C. and 5% $CO_2$ in low-calcium (0.09 mM) SFM (Invitrogen) medium supplemented with 0.25 ng/ml EGF (Invitrogen), 25 µg/ml pituitary extract (Invitrogen) and 25 µg/ml gentamycin (Sigma).

The keratinocytes were then treated for 72 hours with the avocado peptide extract (0.05% DM and 0.005% DM), according to example 1, or by the references: 0.1 µM retinoic acid (Sigma) or 1.5 mM calcium (Prolabo). Two identical series were prepared in order to assay both the release/production of hyaluronic acid and the incorporation of sulfide in the GAGs fraction. The batch corresponding to the assay of the GAGs was supplemented with $^{35}$S-sulfate (Amersham) after 48 hours of culture (labeling during the last 24 hours).

At the end of the treatment, in the batch corresponding to the assay of GAGs, the incorporated radioactivity was counted and thus the variation in the synthesis of GAGs in relation to the control was analyzed.

In the batch corresponding to the assay of hyaluronic acid, at the end of the treatment, the culture supernatants were collected and hyaluronic acid was assayed using a specific modified ELISA test (Biogenic).

Intergroup comparisons were carried out by analysis of variance using Dunnett's multiple comparison test.

1.2. Results:

1.2.1. Effect on the Synthesis of GAGs:

Calcium, used as a reference (pro-differentiating effect) stimulates the incorporation of $^{35}$S-sulfate in the GAGs fraction; this result validates the test.

Treatment with retinoic acid does not significantly modify the synthesis of GAGs by keratinocytes.

The avocado peptide extract causes a significant increase in the synthesis of GAGS (+30%, table 10).

TABLE 10

Synthesis of GAGs by keratinocytes

| | Incorporation of $^{35}$S-sulfate (cpm) | Percentage |
|---|---|---|
| Control cells | 11163 | |
| Calcium | 17753 | +59%** |
| Retinoic acid | 13217 | +18% |
| 0.005% DM avocado peptide extract | 14973 | +34%* |
| 0.05% DM avocado peptide extract | 14833 | +33% |

*p < 0.05;
**p < 0.01: Dunnett's test.

I.2.2. Effect on the Synthesis/Release of Hyaluronic Acid:

Retinoic acid, the test reference, significantly increased the quantity of hyaluronic acid present in the keratinocyte culture supernatants. With no effect on the synthesis of GAGs, retinoic acid specifically stimulates the production of hyaluronic acid.

The 0.005% avocado peptide extract significantly increases the production of hyaluronic acid (+30%) (table 11).

TABLE 11

Synthesis/release of hyaluronic acid by keratinocytes

| | HA (ng/ml) | Percentage |
|---|---|---|
| Control cells | 4684 | |
| Retinoic acid | 11503 | +146%** |
| 0.005% DM avocado peptide extract | 6138 | +31%* |
| 0.05% DM avocado peptide extract | 4924 | +5% |

*p < 0.05;
**p < 0.01: Dunnett's test.

II. Effect on the Neosynthesis of Epidermal Lipids (Refatting Activity)

II.1. Materials:

Day-five reconstructed epidermises (BIOalternatives) were cultured under the following conditions:
control epidermises (R): differentiation medium (BIOalternatives),
control epidermises (T): depleted differentiation medium,
avocado peptide extract (0.005% DM and 0.05% DM), according to example 1, in depleted differentiation medium (systemic application).

II.2. Methods:

The epidermises were placed in 12-well plates under the conditions described above (complete or depleted differentiation medium, containing or not containing the avocado peptide extract).

After 24 hours, the culture medium was refreshed and supplemented with 0.75 µCi/ml $^{14}$C-acetate (Amersham). The epidermises were then incubated for 48 hours at 37° C. and 5% CO2.

After the treatment, the epidermises were washed with PBS (Invitrogen), dissociated from their pods and lysed by 0.5 M perchloric acid on ice.

Lipids were then extracted by a methanol/chloroform solution (2:1). The incorporated radioactivity (corresponding to total lipids) was then quantified by liquid scintillation. After thin-layer chromatography, the lipids were analyzed separately by direct data entry of the radioactivity of the various spots and quantification using a Cyclone PhosphorImager (Packard).

II.3. Results:

II.3.1. Effect on the Synthesis of Total Lipids:

The complete differentiation medium (epidermises R) induced a not significant increase in the incorporation of acetate in the total lipids. The avocado peptide extract does not affect the synthesis of total lipids (table 12).

TABLE 12

Synthesis of total lipids on reconstructed epidermises

| | Incorporation of acetate (cpm) | Percentage |
|---|---|---|
| Epidermises T (depleted medium) | 32171 | |
| Epidermises R (differentiation medium) | 41143 | +28% (NS) |
| 0.005% DM avocado peptide extract | 34705 | +11% (NS) |
| 0.05% DM avocado peptide extract | 35588 | +8% (NS) |

NS: not significant.

11.3.2. Analysis of Lipid Neosynthesis Profiles (Tables 12 and 13):

The complete differentiation medium (epidermises R) induced a change in the phospholipid profile with in particular an increase in phospholipids (+24% in relation to epidermises T) and cholesterol sulfate (+13%). The total quantity of ceramides/cerebrosides is not changed, although a large change in the lipid profiles obtained is observed: an increase in the most polar ceramides/cerebrosides (+38%) and a decrease in the least polar ceramides/cerebrosides (−16%) (table 13). With regard to neutral lipids, the complete differentiation medium induced an increase in cholesterol (+19%), free fatty acids (+37%) and a decrease in esterified fatty acids (−38%) (table 14).

TABLE 13

Lipid profiles in the "phospholipids + sphingolipids" system (% of control T)

| | Sphingo-myelin | Phospho-lipids | Cholesterol sulfate | Polar ceramides/ cerebrosides | Less polar ceramides/ cerebrosides |
|---|---|---|---|---|---|
| Epidermises T (depleted medium) | 100 | 100 | 100 | 100 | 100 |
| Epidermises R (differentiation medium) | 105 | 124 | 113 | 138 | 84 |
| 0.005% DM avocado peptide extract | 90 | 104 | 101 | 130 | 86 |
| 0.05% DM avocado peptide extract | 91 | 112 | 105 | 128 | 83 |

The 0.005% DM and 0.05% DM avocado peptide extracts induce an increase in the most polar ceramides/cerebrosides (+30% and +28% in relation to the epidermises T), a decrease in the least polar ceramides/cerebrosides (−14% and −17%) (table 13) and at 0.05% DM an increase in free fatty acids (+32%) (table 14). These effects are similar to those of the complete differentiation medium.

TABLE 14

Lipid profiles in the "neutral lipids + fatty acids" system (% of control T)

| | Cholesterol | Free fatty acids | Esterified fatty acids |
|---|---|---|---|
| Epidermises T (depleted medium) | 100 | 100 | 100 |
| Epidermises R (differentiation medium) | 119 | 137 | 62 |
| 0.005% DM avocado peptide extract | 112 | 103 | 93 |
| 0.05% DM avocado peptide extract | 107 | 132 | 90 |

III. General Conclusion

A hydrating and refatting effect of the avocado peptide extract was shown. Indeed, the avocado peptide extract stimulates the synthesis of glycosaminoglycans and hyaluronic acid, which are involved in the maintenance of a suitable level of hydration of the skin. Additionally, the avocado peptide extract stimulates the neosynthesis of epidermal lipids, which are involved in the barrier function of the epidermis.

EXAMPLE 4

Cosmetic Formulations Containing the Avocado Peptide Extract

| Cleansing water 1 | |
|---|---|
| Raw material/brand name | % |
| Purified water B4 | Qsp 100% |
| Biosaccharide gum | 1% to 5% |
| Butylene glycol | 1% to 5% |
| Purified saponin | 0% to 1% |
| Rose water | 0% to 1% |
| Avocado peptide extract | 0% to 5% |
| Preservatives | 0% to 1% |
| Allantoin | 0% to 1% |

-continued

| Cleansing water 1 | |
|---|---|
| Raw material/brand name | % |
| Citric acid monohydrate | 0% to 1% |
| Tromethamine | 0% to 1% |

| Cleansing water 2 | |
|---|---|
| Raw material/brand name | % |
| Capryloyl glycine | 0% to 1% |
| Soda lye | 0% to 1% |
| Purified water B4 | 20% to 100% |
| Sequestrant | 0% to 1% |
| Butylene glycol | 1% to 5% |
| Avocado peptide extract | 0% to 5% |
| Octanediol | 0% to 1% |
| PEG-32 | 1% to 5% |
| PEG-7 palmcocoate | 1% to 5% |
| Zinc gluconate | 0% to 1% |
| Citric acid monohydrate | 0% to 1% |
| Purified water B4 | Qsp 100% |
| Fragrance | 0% to 1% |
| Poloxamer 184 | 1% to 5% |
| D.S.B. C SP | 1% to 5% |

| Water-in-oil emulsion | |
|---|---|
| Raw material/brand name | % |
| Liquid isoparaffin | 5% to 20% |
| Isocetyl stearate | 5% to 20% |
| Hydroxystearate Al—Mg | 5% to 20% |
| ABIL WE 09 | 1% to 5% |
| Glycerol | 1% to 5% |
| Thick vaseline oil | 1% to 5% |
| Micronized zinc oxide | 1% to 5% |
| Butylene glycol | 1% to 5% |
| Avocado peptide extract | 0% to 5% |
| Isononyl isononanoat | 1% to 5% |
| White beeswax | 1% to 5% |
| Sodium tartrate | 1% to 5% |
| Sodium chloride | 0% to 5% |
| Glycine | 1% to 5% |
| Octanediol | 0% to 1% |
| Cholesterol | 0% to 1% |
| Phytosphingosine | 0% to 1% |
| Tartaric acid | 0% to 1% |
| Purified water B4 | Qsp 100% |

Oil-in-water emulsion

| Raw material/brand name | % |
| --- | --- |
| Hydrogenated polydecene | 5% to 20% |
| Lauryl glucoside-glystearate | 1% to 5% |
| Dicaprylyl carbonate | 1% to 5% |
| Glycerol | 5% to 20% |
| Carbopol ETD 2020 | 0% to 1% |
| Xanthan gum | 0% to 1% |
| Avocado peptide extract | 0% to 5% |
| Soda lye | 0% to 1% |
| Preservatives | 0% to 1% |
| Citric acid monohydrate | 0% to 1% |
| Purified water B4 | Qsp 100% |

Oil

| Raw material/brand name | % |
| --- | --- |
| Solubilizer | 0% to 1% |
| Sweet almond oil | 5% to 20% |
| Caprylate/copra caprate | Qsp 100% |
| Refined macadamia oil | 5% to 20% |
| Glycerol caprylocaprate | 5% to 20% |
| Alpha bisabolol nat | 0% to 1% |
| Alpha tocopherol | 0% to 1% |
| Avocado peptide extract | 0% to 5% |
| Preservative | 0% to 1% |
| Ester | 0% to 1% |

Milk

| Raw material/brand name | % |
| --- | --- |
| Sweet almond oil | 1% to 5% |
| Corn oil | 1% to 5% |
| Stearic acid | 1% to 5% |
| Cetyl alcohol C16 C18 | 0% to 1% |
| Antifoaming agent 70414 | 0% to 1% |
| Lauryl alcohol 11oe | 1% to 5% |
| PEG 300 monolaurate | 0% to 1% |
| Glycerol monoleate | 0% to 1% |
| Glycerol monostearate | 1% to 5% |
| Avocado peptide extract | 0% to 5% |
| Preservatives | 0% to 1% |
| Citric acid monohydrate | 0% to 1% |
| Trisodium citrate | 0% to 1% |
| Purified water | Qsp 100% |
| Fragrance | 0% to 1% |
| Peanut oil | 1% to 5% |
| Hydrogenated palm oil | 1% to 5% |

Foam

| Raw material/brand name | % |
| --- | --- |
| Purified water B4 | Qsp 100% |
| Lauroamphoacetate | 5% to 20% |
| Cocoglucoside | 5% to 20% |
| Oronal LCG | 5% to 20% |
| Hydriosul KMG 30 (2) | 5% to 20% |
| PEG 6000 distearate | 1% to 5% |
| Preservative | 1% to 5% |
| Avocado peptide extract | 0% to 5% |
| Chamomile extract | 1% to 5% |
| Citric acid monohydrate | 0% to 1% |
| Sequestrant | 0% to 1% |
| Wheat cocoprotein | 0% to 1% |
| Mustiti 11/1 fragrance | 0% to 1% |
| Soda lye | 0% to 1% |

Spray

| Raw material/brand name | % |
| --- | --- |
| Purified water B4 | Qsp 100% |
| Trilaureth-4 phosphate | 1% to 5% |
| Dicaprylyl carbonate | 1% to 5% |
| Butylene glycol | 1% to 5% |
| Erythrityl ester | 1% to 5% |
| Fluid vaseline oil | 1% to 5% |
| Shea butter (liquid) | 0% to 1% |
| Pure jojoba | 0% to 1% |
| Preservatives | 0% to 1% |
| Avocado peptide extract | 0% to 5% |
| Soda lye | 0% to 1% |
| Mustiti 10/3 fragrance | 0% to 1% |
| Xanthan gum | 0% to 1% |
| Carbopol 981 NF | 0% to 1% |
| Sequestrant | 0% to 1% |
| Citric acid monohydrate | 0% to 1% |

The invention claimed is:

1. A method for treating pruritus selected from the group consisting of pruritus gravidarum, psychogenic pruritus and drug-related pruritus comprising the administration of an effective amount of a dermatological composition containing an avocado peptide extract, which contains 2% to 10% by weight of alpha-amino nitrogen in relation to the weight of the dry matter of the peptide extract, and a suitable excipient, to a patient in need thereof.

2. The method of claim 1, wherein the avocado peptide extract is obtainable by a method comprising the following steps:
an avocado oil cake is obtained through drying and extraction of the oil; after which
said oil cake is cold crushed (cryogrinding) and totally delipidated, then decanted, centrifuged and collected; after which
a first hydrolysis is carried out in the presence of glucanases, followed by centrifugation and the elimination of the soluble fraction;
a second hydrolysis is carried out in the presence of one or more proteases, followed by centrifugation and the elimination of the pellet; after which
the peptide phase is concentrated by nanofiltration; followed by
simple filtration (10 μm), then by ultrafiltration (10 kDa cutoff); and finally
packaging.

3. The method of claim 2, wherein the avocado oil cake is obtained from avocado fruit.

4. The method of claim 2, wherein the peptide phase concentrated by nanofiltration is after that decolorized in the presence of activated carbon.

5. The method of claim 2, wherein after the ultrafiltration step and before the packaging step, the process comprises steps of adding a preservative, and a final sterilizing microfiltration (0.2 μm).

6. The method of claim 1, wherein the avocado peptide extract has the following amino acid composition, expressed as a weight percentage in relation to the total weight of the amino acids:

Alanine 6.4-7.8
Arginine 4.7-5.7
Aspartic acid 10.3-12.7
Cystine-cysteine 2.9-3.5
Glutamic acid 13.0-15.8
Glycine 5.3-6.5
Histidine 2.2-2.6
Isoleucine 4.8-5.8
Leucine 7.6-9.4
Lysine 3.0-3.8
Methionine 1.2-1.6
Phenylalanine 4.7-5.7
Proline 4.1-5.2
Serine 5.5-6.7
Threonine 4.6-5.6
Tyrosine 3.6-4.4
Valine 5.8-7.2.

7. The method of claim 1, wherein 50% of the peptides of the extract consist of 10 to 30 amino acids.

8. The method of claim 1, wherein the pruritus is pruritus gravidarum.

9. The method of claim 8, wherein the pruritus gravidarum is selected from the group consisting of obstetric cholestasis and prurigo gravidarum.

10. The method of claim 1, wherein the dermatological composition has hydrating and refatting activity.

11. The method of claim 1, wherein the dermatological composition comprises 0.01% to 20% in dry weight of the avocado peptide extract in relation to the total weight of said drug or dermatological composition.

12. The method of claim 1, wherein the dermatological composition further comprises at least one anti-irritant and/or soothing and/or cicatrizing and/or anti-aging and/or hydrating agent.

13. The method of claim 12, wherein the anti-irritant and/or soothing and/or cicatrizing and/or anti-aging and/or hydrating agent is selected from the group consisting of glycine, plant sugars and/or peptides, lupeol, oxazolines, oxazolidinones, lipoic acid, alpha bisabolol, licorice derivatives, enoxolone, ectoine, avocado furans, *Centella asiatica* extracts, caffeine, retinol, retinal, retinoic acid, zinc oxide, magnesium, silicon, copper, zinc, manganese, selenium, hyaluronic acid, azelaic acid and salts or esters thereof, salicylic acid alpha hydroxy acid (AHA), AHA esters, pyrrolidone carboxylic acid ceramides, cholesterol, squalane, phospholipids, beta carotene, vitamin A, vitamin E, vitamin C, vitamin B3, vitamin B5, vitamin B6, benzoyl peroxide, urea, coenzyme Q10, glucosamine and salts thereof, N-acetyl glucosamine, thermal or spring waters, soy peptides and arabinogalactan.

* * * * *

UNITED STATES PATENT AND TRADEMARK OFFICE
CERTIFICATE OF CORRECTION

PATENT NO. : 8,449,930 B2  
APPLICATION NO. : 13/128109  
DATED : May 28, 2013  
INVENTOR(S) : Philippe Msika et al.

Page 1 of 1

It is certified that error appears in the above-identified patent and that said Letters Patent is hereby corrected as shown below:

IN THE SPECIFICATION

Column 11, line 64, please delete "Rat peritoneal mast cells ($2 \times 10^3$ cells/ml)" and replace with --Rat peritoneal mast cells ($2 \times 10^5$ cells/ml)--.

Column 12, line 46, please delete "for minutes at 37° C." and replace with --for 30 minutes at 37° C."--.

Signed and Sealed this  
Twenty-ninth Day of October, 2013

Teresa Stanek Rea  
*Deputy Director of the United States Patent and Trademark Office*